(12) United States Patent
Han et al.

(10) Patent No.: US 10,632,137 B2
(45) Date of Patent: Apr. 28, 2020

(54) **COMPOSITION CONTAINING IVERMECTIN FOR EXTERMINATING *CLAVINEMA MARIAE* INFECTION ON *SEBASTES SCHLEGELI***

(71) Applicant: REPUBLIC OF KOREA (National Institute of Fisheries Science), Busan (KR)

(72) Inventors: Hyun-Ja Han, Busan (KR); Sung-hee Jung, Busan (KR); Miyoung Cho, Busan (KR); Na Young Kim, Busan (KR); Myoung Sug Kim, Busan (KR); Jeung-Wan Do, Busan (KR); Han-Gil Seo, Busan (KR)

(73) Assignee: REPUBLIC OF KOREA (NATIONAL INSTITUTE OF FISHERIES SCIENCE), Busan (KR)

( * ) Notice: Subject to any disclaimer, the term of this patent is extended or adjusted under 35 U.S.C. 154(b) by 0 days.

(21) Appl. No.: 16/032,602

(22) Filed: Jul. 11, 2018

(65) Prior Publication Data
US 2019/0060342 A1 Feb. 28, 2019

(30) Foreign Application Priority Data
Aug. 30, 2017 (KR) ........................ 10-2017-0110160

(51) Int. Cl.
*A61K 31/7048* (2006.01)
*A61K 9/00* (2006.01)
*A61P 33/10* (2006.01)

(52) U.S. Cl.
CPC ........ *A61K 31/7048* (2013.01); *A61K 9/0053* (2013.01); *A61P 33/10* (2018.01)

(58) Field of Classification Search
None
See application file for complete search history.

(56) References Cited

FOREIGN PATENT DOCUMENTS

| CN | 103372211 A | 10/2013 |
|---|---|---|
| DE | 102008011800 A1 * | 10/2009 |
| EP | 0214731 B1 | 1/1991 |
| KR | 20080080667 A | 9/2008 |
| KR | 20130062333 A | 6/2013 |
| WO | WO2012177881 A1 | 12/2012 |

OTHER PUBLICATIONS

Machine translation of DE102008011800A1, Braun, S. et al., published Oct. 2009 (Year: 2009).*
Enden, E. van den, Expert Opinion on Pharmacotherapy, "Pharmacotherapy of helminth infection", 2009, vol. 10, No. 3, pp. 435-451 (Year: 2009).*
Johnson, S.C., Diseases of Aquatic Organisms, "Efficacy of ivermectin for control of the salmon louse *Lepeophtheirus salmonis* on Atlantic salmon", 1993, vol. 17, pp. 101-105 (Year: 1993).*
Chae, J., et al., "Clinical Parasitology", "Seoul National University Publishing Council", , pp. 1-12.
Chae, J., et al., "Clinical Parasitology", "Seoul National University Publishing Council", , pp. 1-12; English Translation.
Iosifidou, E.G., et al., "Depletion Study of Fenbendazole in Rainbow Trout (*Oncorhynchus mykiss*) After Oral and Bath Treatment", "Aquaculture", 1997, pp. 191-199, vol. 154.
Ministry of Oceans and Fisheries, "Aquatic Anthelmintic Approved in the Country", "Summarized Terminology Book of Aquatic Medicine: Aquatic Medicine Catalog", 2016, pp. 1-9.
Ministry of Oceans and Fisheries, "Aquatic Anthelmintic Approved in the Country", "Summarized Terminology Book of Aquatic Medicine: Aquatic Medicine Catalog", 2016, pp. 1-9; English Translation.
Moravec, F., et al., "*Philometra dissimillis* n. sp. From the Ovary of Johnius Belangerii (Sciaenidae) and Other New Records of Philometrids (Nematoda: Philometridae) From Fishes of the Bay of Bengal, India", "Helminthologia", 2016, pp. 133-141, vol. 53, No. 2.
Han, H., et al., "First Report of Clavinema Mariae (Nematoda: Philometridae) in Cultured Rockfish, *Sebastes schlegeli*, in Cheonsuman (Bay), The Republic of Korea", "Korean J Parasitol", Apr. 2017, pp. 219-224, vol. 55, No. 2.
Seo, H., et al., "A Nematode Infection in the Epithelial Tissue of Cultured Rockfish *Sebastes schlegeli* in Cheonsu Bay, Western Korea", "Kor J Fish Aquat Sci", Oct. 2014, pp. 603-610, vol. 47, No. 5.
Canga, A.G., et al., "The Pharmacokinetics and Metabolism of Ivermectin in Domestic Animal Species", "The Veterinary Journal", 2009, pp. 25-37, vol. 179, No. 1.

* cited by examiner

*Primary Examiner* — Layla D Berry
*Assistant Examiner* — Bahar Craigo
(74) *Attorney, Agent, or Firm* — Hultquist, PLLC; Steven J. Hultquist (57) ABSTRACT

The present invention relates to a composition containing Ivermectin for exterminating *Clavinema mariae* infection on *Sebastes schlegeli*, and more specifically, to a composition for exterminating *Clavinema mariae* infection on *Sebastes schlegeli*, containing Ivermectin as an active ingredient, and a method for exterminating *Clavinema mariae* infection by orally administering Ivermectin to *Sebastes schlegeli*. The composition and the exterminating method according to the present invention are excellent in an effect of exterminating *Clavinema mariae* infection of *Sebastes schlegeli*, are safe without causing any side effects on the *Sebastes schlegeli*, and are able to achieve oral administration to thereby be useful in the aquaculture industry.

5 Claims, 5 Drawing Sheets
(5 of 5 Drawing Sheet(s) Filed in Color)

COMPOSITION CONTAINING IVERMECTIN FOR EXTERMINATING *CLAVINEMA MARIAE* INFECTION ON *SEBASTES SCHLEGELI*

CROSS-REFERENCE TO RELATED APPLICATION

The priority of Korean Patent Application 10-2017-0110160 filed Aug. 30, 2017 is hereby claimed under the provisions of 35 USC § 119. The disclosure of Korean Patent Application 10-2017-0110160 is hereby incorporated herein by reference, in its entirety, for all purposes.

TECHNICAL FIELD

The present invention relates to a composition containing Ivermectin for exterminating *Clavinema mariae* infection on *Sebastes schlegeli*, and more specifically, to a composition for exterminating *Clavinema mariae* infection on *Sebastes schlegeli*, containing Ivermectin as an active ingredient, and a method for exterminating *Clavinema mariae* infection by orally administering Ivermectin to *Sebastes schlegeli*.

BACKGROUND ART

*Sebastes schlegeli* is an important fish species to represent domestic marine aquaculture together with an olive flounder in Korea, and is an ovoviviparous fish species in which the body and fins are a brown color and the stomach is a gray color. The *Sebastes schlegeli* lives in a reef area of 10 to 100 m in depth and inhabits the northwest Pacific region of the Korean coast, Japan and China, and the like. At the beginning of the cultivation, an amount of sea surface fishery was larger than that of aquaculture production. However, since the late 1990s, the amount of aquaculture production has increased sharply, and the production amount increased to 35,564 tons in 2007 and accounted for 32.5% of total aquaculture production in 2013. However, since then, a production rate has slightly decreased, and the production amount was 18,774 tons in 2015, which accounted for about 22% of the aquaculture production in Korea (KOSIS, 2016).

As described above, the *Sebastes schlegeli*, has an important position in view aquaculture species; however, *Sebastes schlegeli* produced by the farms are dying due to frequent diseases over the course of the year and rapid changes in the breeding environment. *Flexibacter*, Streptococcus, *Vibrio*, and the like, have been reported as bacteria that infect the *Sebastes schlegeli*, and infection of red sea bream irido virus (RSIV), viral hemorrhagic septicaemia virus (VHSV), nervous necrosis virus (NNV), and Lymphocystis have been reported as viral diseases. Infection of Microcotyle, Epitheliocystis, Benedenia, Trichodina, Scutica and Caligus, and the like, as a parasite has been reported.

Recently, a Philometridae nematode parasitic disease on the epithelium such as fins, cephalus, or the like, of the *Sebastes schlegeli*, has been reported. Particularly, the present inventors have identified parasites that infect the *Sebastes schlegeli* at a molecular biological level by targeting 18S rRNA and COI (Cytochrome c oxidase subunit I) gene, and identified morphologically up to a species classification level, and as a result, finally confirmed the parasite as the *Clavinema mariae*. The *Clavinema mariae* was first isolated in the fins of a Pleuronectes schrenki in 1930 and was reported as *Philometra mariae* at that time. Machida later found the parasite in the fins and operculum of right-eyed flounder and *Limanda yokohamae*, and asserted to reclassify the parasite as *Clavinema* genus, and it was reclassified as *Clavinema mariae* by Margolis and Moravec. There are no cases of infection with *Clavinema mariae* in aquaculture fish except for a case of infection with *Clavinema mariae* in the aquaculture of *Sebastes schlegeli* in Korea, and all infections were reported on wild fish. In addition, there are no examples of attempts to treat the infections with *Clavinema mariae* of fish.

The infection itself with *Clavinema mariae* on the *Sebastes schlegeli* does not cause direct death of the fish. However, when the fish is infected, it is confirmed that the fish is infected by a secondary pathogenic bacteria through wounds caused when larvae become adults and escape from the life span of the fish, and the infected fish dies. Since the death due to the *Clavinema mariae* on the west coast of Cheonsu Bay area was first reported in 2012, the deaths due to the *Clavinema mariae* continuously occur in the summer season, causing serious damage.

Under these technical backgrounds, the present inventors have made intensive efforts to develop an anthelmintic having secured safety capable of exterminating the infection with *Clavinema mariae* on the *Sebastes schlegeli*. As a result, it was confirmed that among various candidate materials, Ivermectin was particularly safe for fish and had an excellent exterminating effect, and completed the present invention.

Related Art Document (Patent Document 1) European Patent Publication No. 0214731

Non-Patent Documents (Non-Patent Document 1) Seo, H. G. et al. 2014. A nematoda infection in the Epithelial Tissue of Cultured Rockfish *Sebastes schlegeli* in Cheonsu Bay, Western Korea. Kor J Fish Aquat Sci 47(5), 603-610. http://dx.doi.org/10.5657/KFAS.2014.0603

(Non-Patent Document 2) Han, H, J. et al. 2017. First report of *Clavinema mariae* (Nematoda: Philometridae) in cultured rockfish, *Sebastes schlegeli*, in Cheonsuman (Bay), Republic of Korea. Korean Journal of Parasitology 55(2), 219-224.

DISCLOSURE

Technical Problem

An object of the present invention is to provide a novel composition and feeds for exterminating *Clavinema mariae* infection on *Sebastes schlegeli*.

Another object of the present invention is to provide a novel method for exterminating or preventing *Clavinema mariae* infection on *Sebastes schlegeli*.

Technical Solution

In order to achieve the foregoing objects, the present invzention provides a composition for exterminating *Clavinema mariae* infection on *Sebastes schlegeli*, comprising Ivermectin as an active ingredient.

The present invention also provides feeds for exterminating *Clavinema mariae* infection on *Sebastes schlegeli*, comprising Ivermectin as an active ingredient.

Further, the present invention provides a method for exterminating *Clavinema mariae* infection on *Sebastes*

*schlegeli* comprising a step of administering the composition or the feeds to *Sebastes schlegeli*.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

As far as it is not defined in other ways, all technical and scientific terms used in the present specification have the same meaning as being generally appreciated by those skilled in the art to which the present invention pertains. In general, the nomenclature used in the present specification is well known in technical fields and generally used.

In order to develop an anthelmintic capable of exterminating *Clavinema mariae* infection on *Sebastes schlegeli*, the present inventors conducted various literature investigations including medicines licensed for livestock. Consequently, a total of nine candidate materials were selected as shown in Table 1 below, and a killing effect on *Clavinema mariae* was measured for each concentration with respect to nine candidate materials, and as a result, it could be confirmed that Ivermectin effectively exterminated the *Clavinema mariae* in vivo as well as in vitro.

Accordingly, in an aspect, the present invention relates to a pharmaceutical composition for exterminating *Clavinema mariae* infection on *Sebastes schlegeli*, comprising Ivermectin as an active ingredient.

European Patent Publication No. 0214731 discloses Ivermectin, which is one of avermectin-based compounds, and Ivermectin has been evaluated as the best drug after benzimidazole-based anthelmintic, and is a compound that exhibits potent efficacy against a wide variety of parasites that are parasitic on crops and soils as well as extracorporeal and intracorporeal parasites that are parasitic on mammals. In addition, due to its excellent safety, it is widely used in large animal and medium and small animal clinics in Korea at present.

Avermectin is a collective name of a novel macrocyclic lactone-based material that is effective in exterminating nematodes, ticks, insects, and the like, and *Streptomyces avermitilis*, a soil actinomycetes producing this material, was first isolated from a soil sample.

It is known as a substrate for avermectin, one of the avermectin-based compounds, which is composed of at least 83% of avermectin $B_{1a}$ and below 20% of $B_{1b}$. An action mechanism of avermectin is known to enhance a signaling pathway leading to release of gamma amino butyric acid (BABA) in peripheral nerves of nematodes and arthropods, paralyzing the peripheral nerves of the worms. In humans, it is reported that the avermectin reaches the maximum plasma concentration at 4 hours after oral administration, 0.5 to 2.0% is excreted as urine, the rest is excreted as feces, and the half-life is about 16 hours (Clinical Parasitology 2011).

Ivermectin has been known to be effective in intracorporeal parasites such as oesophagostomiasis, strongyloides ransomi, lung worm, roundworm, stomach worm, and the like, and extracorporeal parasites such as mites, caterpillars, and ticks, in various animals including cattle, pigs, sheep, etc. However, it has not yet been reported that Ivermectin is usable for exterminating *Clavinema mariae* infection on *Sebastes schlegeli*.

In the present invention, the term "active ingredient" means to include a main component as a material or a group of materials to be expected to directly or indirectly express the efficacy and effects of the drug by an inherent pharmacological action.

The composition for exterminating *Clavinema mariae* infection on *Sebastes schlegeli*, containing Ivermectin of the present invention as an active ingredient may be a pharmaceutical preparation, and the pharmaceutical preparation of the present invention may be administered together with a pharmaceutically acceptable carrier. In oral administration, a binder, a lubricant, a disintegrant, an excipient, a solubilizing agent, a dispersing agent, a stabilizer, a suspending agent, a coloring matter, a flavoring, and the like may be further included in addition to the active ingredient. In the case of an injection, the pharmaceutical preparation of the present invention may be mixed with a buffer, a preservative, an anhydrous agent, a solubilizer, an isotonic agent, a stabilizer, and the like. In addition, at the time of topical administration, the pharmaceutical preparation of the present invention may be used with a base, an excipient, a lubricant, a preservative, and the like.

A formulation of the pharmaceutical preparation of the present invention may be prepared in various ways by mixing with a pharmaceutically acceptable carrier as described above, and particularly, may be prepared as a preparation for oral administration.

In another aspect, the present invention relates to a feed additive composition. A component included in the feed additive composition of the present invention includes components conventionally used in feed additive compositions in addition to Ivermectin as an active ingredient, and may include various known functional materials for feed additive such as a growth promoting material, an immune enhancing material, and the like.

The feed additive composition of the present invention may be formulated into any formulation conventionally produced in the art, and may be formulated, for example, as a solution, a suspension, an emulsion, an oil or a powder, but is not limited thereto.

In still another aspect, the present invention relates to a method for exterminating *Clavinema mariae* infection comprising a step of administering the composition or the feed containing Ivermectin as an active ingredient to *Sebastes schlegeli*.

In the present invention, the administration is preferably oral administration, but is not limited thereto.

In other words, the composition of the present invention is able to be administered orally or parenterally, and the route of administration according to the present invention may be oral administration, intramuscular injection, intraperitoneal injection, topical administration, medicated bath (immersion) administration, but is not limited thereto. For the clinical administration as described above, the pharmaceutical composition of the present invention may be prepared as an appropriate formulation by a known technology.

In the present invention, a preferable dose concentration of Ivermectin is 0.5 ppm or more to 2.5 ppm or less, more preferably 1 ppm or more to 2 ppm or less, but is not limited thereto.

In the present invention, the Ivermectin is preferably administered at intervals of 1 to 3 days when administered at a concentration of 0.5 ppm or more to less than 1.5 ppm, and preferably administered at intervals of 2 to 3 days when administered at a concentration of 1.5 ppm or more to 2.5 ppm or less, but is not limited thereto.

An effective dose in the present invention may have a various range depending on the size, mass, administration time, administration method, health condition, severity of disease, and the like of the fish to be treated, and may be determined by those skilled in the art.

The composition and the exterminating method of the present invention may be used alone or in combination with methods using other medications and biological response modifiers in order to exterminate the *Clavinema mariae* infection.

Hereinafter, the present invention is described in detail with reference to Examples. These Examples are only provided to specifically explain the present invention, and it will be obvious to those skilled in the art that the technical scope of the present invention is not construed to be limited to these Examples.

Example 1

In Vitro Experiment for Screening Candidate Material for Exterminating *Clavinema mariae* Infection on *Sebastes schlegeli*

Figure 1:
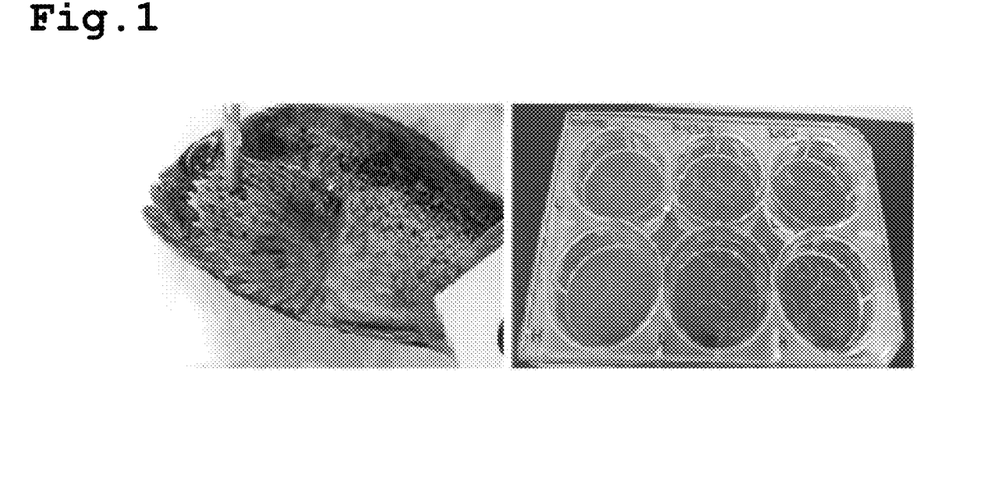
FIG. 1 shows *Sebastes schlegeli* (left) infected by *Clavinema mariae*, and in vitro experiment results (right) for testing effects of candidate materials for exterminating *Clavinema mariae* infection.

Candidate materials of a medicine for exterminating *Clavinema mariae* infection on *Sebastes schlegeli* were screened by examining various documents (Table 1). The *Sebastes schlegeli* is not artificially infected with *Clavinema mariae*, and thus *Sebastes schlegeli* that was naturally infected with *Clavinema mariae* was screened and used for the experiment. From the *Sebastes schlegeli* naturally infected with *Clavinema mariae*, the *Clavinema mariae* was carefully removed with tweezers, preserved in PBS, and directly exposed to nine candidate materials at various concentrations to evaluate the antiparasitic effect. The extracted *Clavinema mariae* survives for several days in PBS and moves freely (FIG. 1). However, after being killed, the movement disappears, and thus whether it is dead or not is able to be easily determined by observing whether it moves or not. Among the nine candidate materials, Febendazole, Pyrantel, Levamisole, Piperazine, Ivermectin, Trichlorfon, and Praziqantel were purchased from Sigma Aldrich (USA), and hydrogen peroxide and formalin solution were purchased from Junsei (Japan). Among the candidate materials, a poorly soluble compound, Febendazole, was dissolved in 100% ethanol and diluted with PBS to be used. Piperazine and Ivermectin were dissolved in dimethylsulfoxide (DMSO) and diluted with PBS to be used.

TABLE 1

| No | Candidates | Effect | Demestic Permission for fishery use |
|---|---|---|---|
| 1 | Fenbendazole | Extermination of nematode, lungworm, kidney worm in livestock | x |
| 2 | Pyrantel | Extermination of roundworm, hookworm, threadworm in livestock | x |
| 3 | Levamisole | Extermination of lungworm, roundworm, nematode in livestock | x |
| 4 | Piperazine | Extermination of roundworm, threadworm, heartworm, nodular worm in livestock | x |
| 5 | Ivermectin | Extermination of ematode, lungworm, extracorporeal parasite in livestock | x |
| 6 | Praziquantel | Extermination of *Microcotyle sebastis* infection in *Sebastes schlegelii* | o |
| 7 | Formaline | Extermination of extracorporeal parasite in flat fish | o |
| 8 | Trichlorfon | Treatment of parasitic disease in carp and japanese eel | o |
| 9 | Hydrogen peroxide | Extermination of extracorporeal parasite in flat fish | o |

Figure 2:
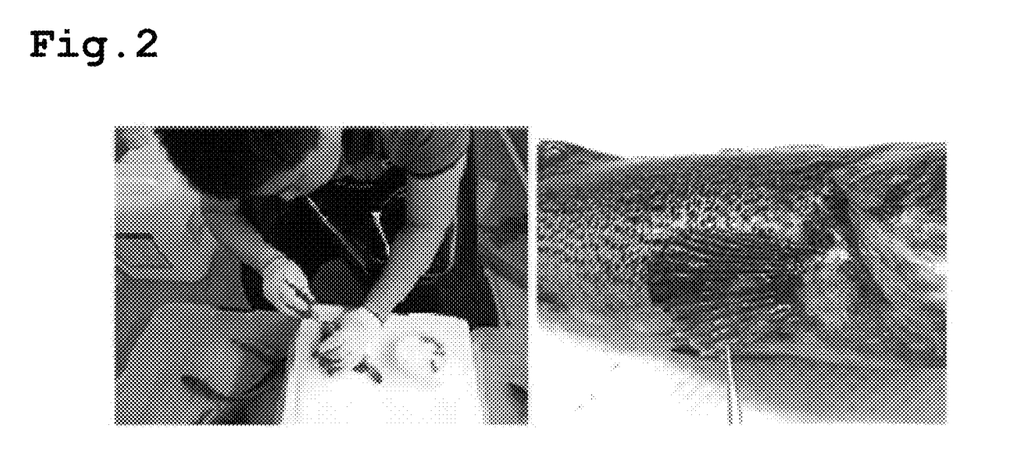
FIG. 2 shows an oral administration process (left) for confirming in vivo the effects of the candidate materials for exterminating *Clavinema mariae* infection on *Sebastes schlegeli* infected, and formation (right) of pus according to an antiparasitic effect after 2 weeks from administration of Ivermectin among the candidate materials for exterminating *Clavinema mariae* infection.
Figure 3:
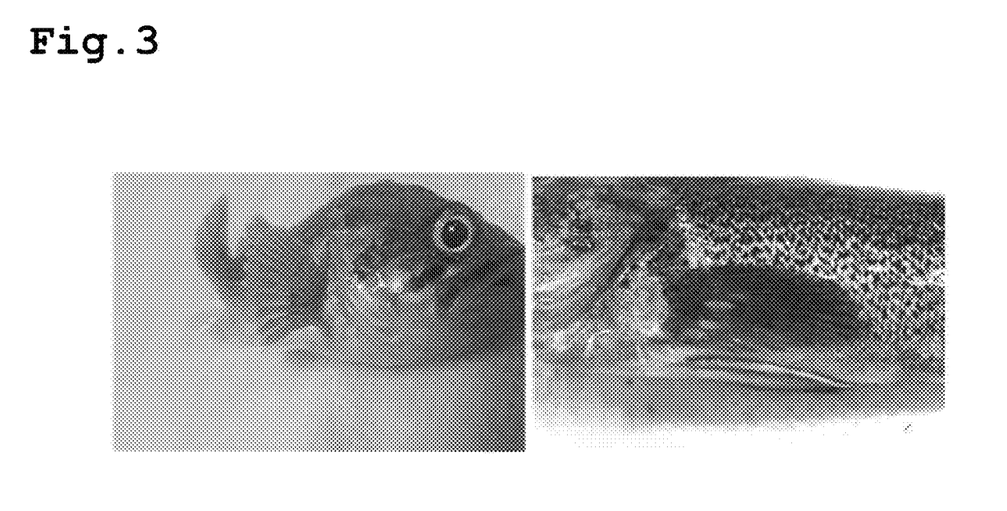
FIG. 3 shows states of *Sebastes schlegeli* after 2 weeks (left) and 6 weeks (right) from Ivermectin administration according to in vivo experiments.
Figure 4A:
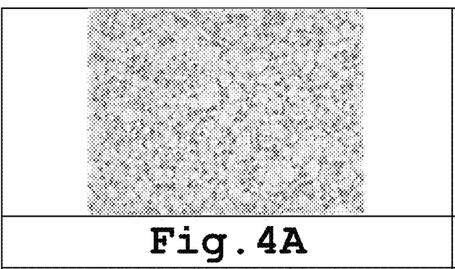
FIGS. 4A-4R are images of histological tissue samples showing the effect of Ivermectin administration.
Figure 4B:
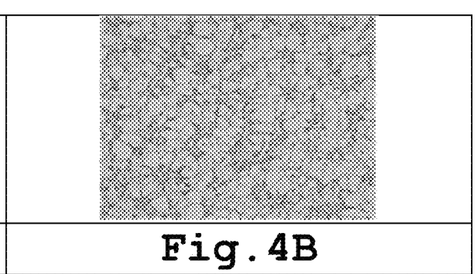
Figure 4C:
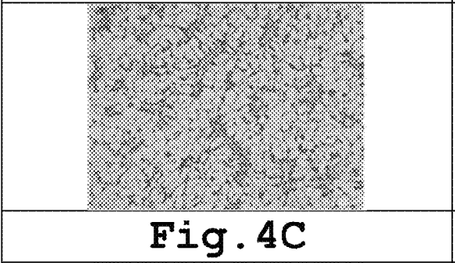
Figure 4D:
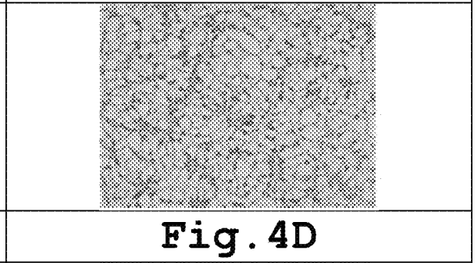
Figure 4E:
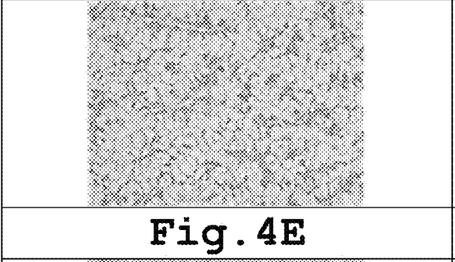
Figure 4F:
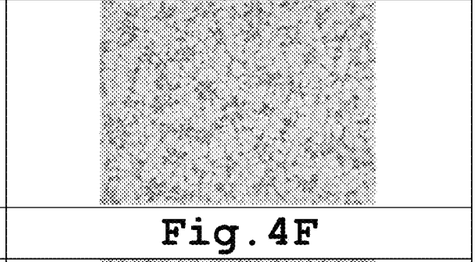
Figure 4G:
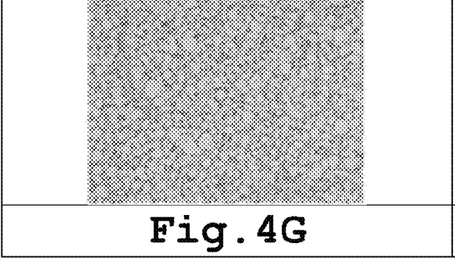
Figure 4H:
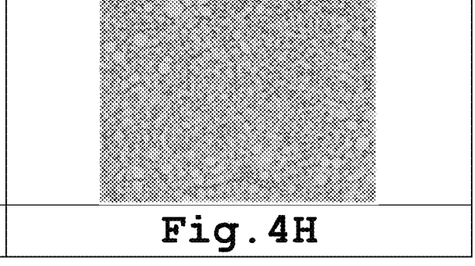
Figure 4I:
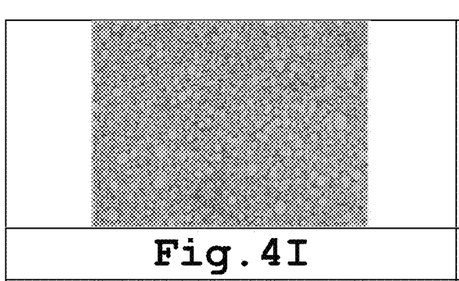
Figure 4J:
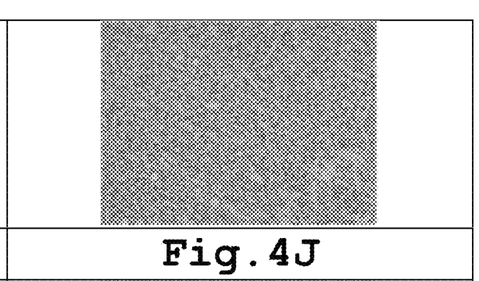
Figure 4K:
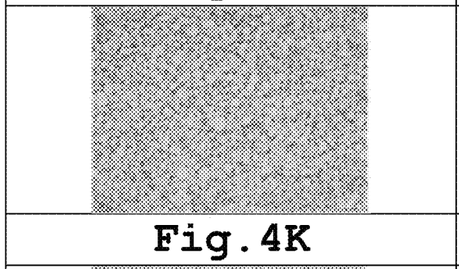
Figure 4L:
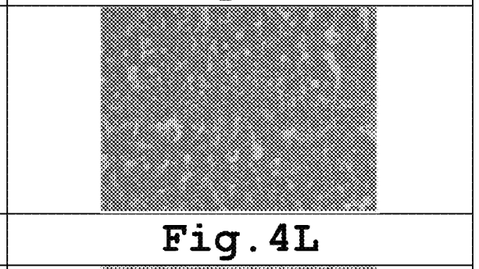
Figure 4M:
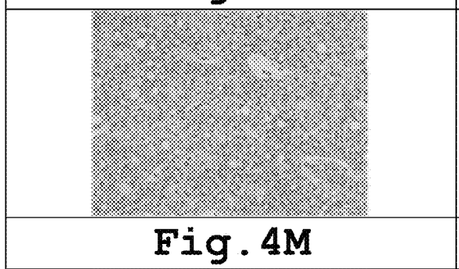
Figure 4N:
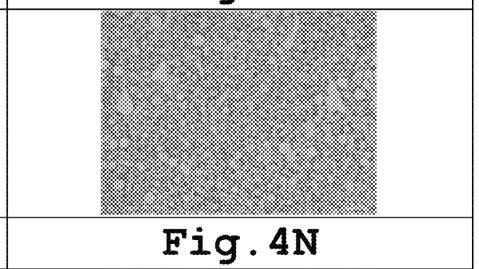
Figure 4O:
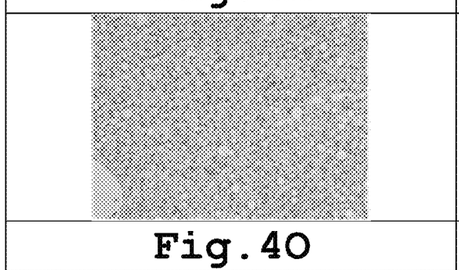
Figure 4P:
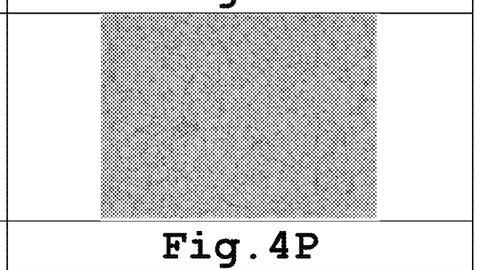
Figure 4Q:
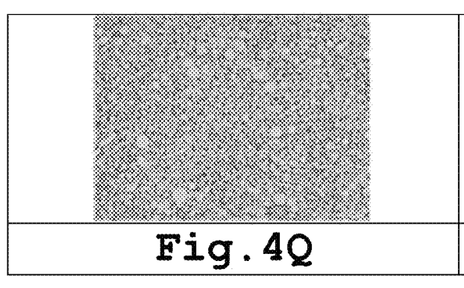
Figure 4R:
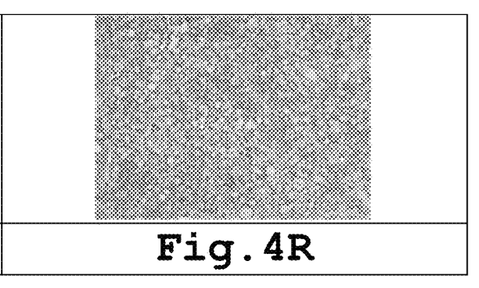

*Clavinema mariae* was extracted from *Sebastes schlegeli* (average weight: 150 g) cultivated on the west coast of Cheonsu Bay area (FIG. 1), 2 ml of each candidate material diluted with PBS to have each concentration was dispensed into a 6-well plate. Ten (10) living *Clavinema mariae* were placed in each well, and viability thereof was confirmed after 1 hour (FIG. 2). In order to identify the most effective compound for exterminating *Clavinema mariae* infection on *Sebastes schlegeli*, recommended concentrations for human, livestock, and fish (Table 2) and killing concentration (Table 3) in *Clavinema mariae* on *Sebastes schlegeli* were compared.

TABLE 2

| Classification | Candidates | Dosing concentration (ppm) | | | |
|---|---|---|---|---|---|
| Oral Preparations | Fenbendazole | 30 | 15 | 5 | 1.7 |
| | | Dead (100%) | Dead (100%) | Survived | Survived |
| | Pyrantel | 0.9 | 0.09 | 0.06 | 0.02 |
| | | Dead (100%) | Dead (100%) | Dead (20%) | Survived |
| | Levamisole | 1.7 | 1 | 0.5 | 0.17 |
| | | Dead (100%) | Dead (100%) | Dead (20%) | Survived |
| | Piperazine | 100 | 75 | 50 | 33 |
| | | Dead (100%) | Dead (100%) | Dead (100%) | Survived |
| | Ivermectin | 0.5 | 0.05 | 0.01 | 0.001 |
| | | Dead (100%) | Dead (100%) | Dead (100%) | Survived |
| | Praziquantel | 1600 | 800 | 400 | 200 |
| | | Dead (100%) | Dead (100%) | Survived | Survived |

TABLE 2-continued

| Classification | Candidates | Dosing concentration (ppm) | | | |
|---|---|---|---|---|---|
| Medicated bath preparations | Formaline | 350 Dead (100%) | 70 Dead (100%) | 50 Dead (100%) | 25 Dead (100%) |
| | Trichlorfon | 75 Dead (100%) | 50 Dead (100%) | 25 Survived | 2.5 Survived |
| | Hydrogen peroxide | 280 Dead (100%) | 14 Dead (100%) | 10 Dead (100%) | 5 Death (100%) |

TABLE 3

| | Oral Preparations | | | | | Medicated bath preparations | | |
|---|---|---|---|---|---|---|---|---|
| Candidates | FB  PR | LV | PP | IV | PZ | FM | TC | HP |
| Recommended concentration (ppm) | $0.1^3$    $5\text{-}10^1$ | $2.5^1$ | $75^1$ | $0.15\text{-}0.2^1$ | $0.2\text{-}0.4^2$ | $100\text{-}200^2$ | $20\text{-}24^2$ | $100\text{-}200^2$ |
| Killing Concentration (ppm) | 5-15  0.02-0.06 | 0.5-0.17 | 33-50 | 0.001-0.01 | 400-800 | 25 | 25-50 | <5 |

*FB, Fenbendazole;
PR, Pyrantel;
LV, Levamisole;
PP, Piperazine;
IV, Ivermectin;
PZ, Praziquantel;
TC, Trichlorfon;
FM, Formalin,
HP, Hydrogen peroxide
[1]Source: Clinical Parasitology Jong-il Chae, Jan. 25, 2011., Seoul National University Publishing Cultural Center
[2]Source: 2016 Medicines for fisheries product summary explanation, National Fisheries Research and Development Institute
[3]Source: 1997 Aquaculture 154, 191-199. Depletion study of fenbendazole in rainbow trout (Oncorhynchus mykiss) after oral and bath treatment, Isofidou E. G., Haagsama N., Tanck M. W. T., Boon J. H., Olling M.

As shown in Table 3, Pyrantel, Levamisole, Piperazine, and Ivermectin which are oral preparations, and Formalin and Hydrogen peroxide which are medicated bath preparations showed an antiparasitic effect of *Clavinema mariae* at a lower concentration than the recommended concentration in vitro experiment, and thus additional in vivo experiments were performed. The Praziquantel did not show the antiparasitic effect of *Clavinema mariae* at a concentration 2000 times higher than the recommended concentration, and the trichlorfon showed the antiparasitic effect at a very high concentration, and thus these preparations were excluded from the subsequent in vivo experiment targets.

Example 2

In Vivo Effect Experiment of Drug for Exterminating *Clavinema mariae* Infection on *Sebastes schlegeli*

500 *Sebastes schlegeli* (116±17 g, 20±9 cm) on the west coast region of Korea were purchased and were allowed to habituate at a water temperature of 18.5 to 21° C. in a sea water tank for one week. Since the *Sebastes schlegeli* infected with *Clavinema mariae* is able to be confirmed by visual inspection, the *Sebastes schlegeli* was anesthetized with MS-222, and only the *Sebastes schlegeli* infected with *Clavinema mariae* was screened by visual inspection and used for clinical examination. In the experienced *Sebastes schlegeli*, it was shown to be infected with 14.4 *Clavinema mariae* on average per one *Sebastes schlegeli*.

For each experimental group, 10 *Sebastes schlegeli* infected with *Clavinema mariae* were used, and febendazole, pyrantel, levamisole, piperazine and Ivermectin were orally administered by the method of Table 4. For the oral administration, a predetermined amount of each candidate material was mixed with blended powder feed to prepare a feed pellet, the *Sebastes schlegeli* was anesthetized, and the feed pellet was inserted up to the stomach with tweezers (FIG. 2). The administration of the medicated bath preparation was conducted by performing medicated bath using formalin and hydrogen peroxide for 10 minutes at each concentration. In order to confirm the safety of the candidate material, mortality was observed for 2 weeks during the experiment. After 2 weeks, all experimental fishes were anesthetized with MS-222, and *Clavinema mariae* was extracted with tweezers to confirm the death. The control group was anesthetized, and then only feed pill to which the drug is not added was orally administered thereto.

TABLE 4

| Classification | Candidates | Dosing concentration (ppm) | Number of administraion/ bath (times) | Killing Effect (%) | Death of Fish (%) |
|---|---|---|---|---|---|
| Oral preparations | Fenbendazole | 5 | 1 | 0 | 0 |
|  |  | 15 | 1 | 0 | 0 |
|  | Pyrantel | 2.7 | 1 | 0 | 0 |
|  | Levamisole | 2.5 | 1 | 0 | 0 |
|  |  | 5 | 1 | 0 | 0 |
|  | Piperazine | 100 | 1 | 0 | 0 |
|  |  | 300 | 1 | 0 | 30 |
|  | Ivermectin | 1 | 1 | 20 | 0 |
| Medicated bath preparations | Formaline | 50 | 1 | 0 | 0 |
|  |  | 200 | 1 | 0 | 0 |
|  | Hydrogen peroxide | 10 | 1 | 0 | 0 |
|  |  | 50 | 1 | 0 | 0 |
| Control Group | — | — | — | 0 | 0 |

As a result, the medicated bath preparations, formalin and hydrogen peroxide could not be confirmed to have the antiparasitic effect against *Clavinema mariae* on *Sebastes schlegeli*. After two weeks from once administration of 1 ppm Ivermectin among the oral preparations, it could be confirmed that some individuals had pus in a spot infected with the *Clavinema mariae*, and showed the antiparasitic effect. Meanwhile, the spot where the pus is formed disappeared within 6 weeks and it was completely cured. It was confirmed that other candidate materials, febendazole, pyrantel, levamisole, and piperazine were orally administered at concentrations shown in Table 4, the antiparasitic effect against *Clavinema mariae* on *Sebastes schlegeli* was not shown at all.

Example 3

Determination of Ivermectin Administration Method for Exterminating *Clavinema mariae* Infection on *Sebastes schlegeli*

It was confirmed through the in vivo experiment of Example 2 that Ivermectin was the only candidate material exhibiting the antiparasitic effect against infection with *Clavinema mariae* on *Sebastes schlegeli*. Accordingly, an administration method for maximizing the antiparasitic effect was confirmed. For this purpose, 10 *Sebastes schlegeli* infected with *Clavinema mariae* were divided for each experimental group, and when two weeks passed after the Ivermectin was administered a total of 1 to 4 times daily or every 2 to 4 days while changing an oral administration concentration from 1 to 18 ppm, the antiparasitic effect and the mortality of the *Clavinema mariae* were observed.

TABLE 5

| Compound | Dosing concentration (ppm) | Dosing times (times) | Dosing intervals | Killing effect (%) | Death of fish (%) |
|---|---|---|---|---|---|
| Ivermectin | 1 | 4 | 2-3 days | 100 | 0 |
|  | 1 | 4 | everyday | 100 | 0 |
|  | 2 | 4 | 2-3 days | 100 | 0 |
|  | 2 | 4 | everyday | 100 | 20 |
|  | 3 | 2 | 3 days | 100 | 20 |
|  | 3 | 2 | everyday | 100 | 60 |
|  | 4 | 2 | everyday | 100 | 60 |
|  | 5 | 2 | everyday | 100 | 30 |
|  | 6 | 2 | 4 days | 100 | 70 |
|  | 18 | 1 | — | — | 100 |

During the experiment, in the experimental group administered at 3 ppm or more of Ivermectin, death occurred after being administered 2 times, and the administration was stopped when strange swimming or death occurred. When 1 to 2 ppm of Ivermectin was administered 4 times, the pus was formed and 100% nematode antiparasitic effect was shown. After 6 weeks, the infection area was cleanly treated. However, when 2 ppm of Ivermectin was administered 4 times, it was confirmed that some *Sebastes schlegeli* were sitting on the bottom and died. The death also occurred at a concentration of 3 ppm or more of Ivermectin. When 18 ppm of Ivermectin was administered, 100% of the *Sebastes schlegeli* died by only one administration. From these results, it could be appreciated that administration of Ivermectin 4 times at a concentration of 1 to 2 ppm is the most effective administration method in consideration of the antiparasitic effect and mortality.

Example 4

Stability Test According to Ivermectin Administration to *Sebastes schlegeli*

Ivermectin was orally administered to *Sebastes schlegeli* according to dosing concentrations, dosing times, and dosing intervals described in Table 6, and after one week from the last oral administration, histological analysis of internal organs was performed. The histological analysis was performed by fixing the liver, kidney, spleen and gill of the experimental fish with 10% neutral formalin, followed by dehydration and paraffin embedding, and the cut tissues were stained with hematoxylin-eosin (H & E) and examined. As a result of histopathological examination, the spleen, kidney, and gill except the liver were normal in all tissues as compared with the control group. Abnormality of the liver tissue was not confirmed in a group in which 1 ppm of Ivermectin was administered 4 times daily or every 2 to 3 days and a group in which 2 ppm of Ivermectin was administered every 2 to 3 days, but hepatocyte metamorphosis, vacuolar formation, or the like, was confirmed in a group in which 2 ppm of Ivermectin was administered daily, and the hepatocyte metamorphosis, vacuolar formation, or the like, was confirmed in all groups in which 2 ppm or more of Ivermectin was administered. Therefore, it was confirmed that administration of 1 ppm of Ivermectin 4 times daily or every 2 to 3 days or administration of 2 ppm of Ivermectin every 2 to 3 days was the most preferable administration method in view of stability.

TABLE 6

| Dosing concentration (ppm) | Dosing times | Dosing intervals | Liver of subject 1 Figure No. | Liver of subject 2 Figure No. | hepatocyte |
|---|---|---|---|---|---|
| 1 | 4 | 2-3 days | 4A | 4B | Normal |
| 1 | 4 | everyday | 4C | 4D | Normal |
| 2 | 4 | 2-3 days | 4E | 4F | Normal |
| 2 | 4 | Everyday | 4G | 4H | hepatocyte metamorphosis, vacuolar formation |
| 3 | 2 | 3 days | 4I | 4J | hepatocyte metamorphosis, vacuolar formation |
| 3 | 2 | Everyday | 4K | 4L | hepatocyte metamorphosis, vacuolar formation |
| 4 | 2 | Everyday | 4M | 4N | hepatocyte metamorphosis, vacuolar formation |
| 5 | 2 | Everyday | 4O | 4P | hepatocyte metamorphosis, vacuolar formation |
| 6 | 2 | 4 days | 4Q | 4R | hepatocyte metamorphosis, vacuolar formation |

The composition and the exterminating method according to the present invention are excellent in an effect of exterminating *Clavinema mariae* infection on *Sebastes schlegeli*, are safe without causing any side effects on the *Sebastes schlegeli*, and are able to achieve oral administration to thereby be useful in the aquaculture industry.

Although specific embodiments of the present invention are described in detail as described above, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A method for exterminating *Clavinema mariae* infection on *Sebastes schlegeli*, comprising administering to *Sebastes schlegeli* a composition comprising ivermectin as an active ingredient or a feed comprising ivermectin as an active ingredient.

2. The method of claim 1, wherein the administration comprises oral administration.

3. The method of claim 2, wherein ivermectin is administered at a concentration of 0.5 ppm to 2.5 ppm.

4. The method of claim 3, wherein ivermectin is administered at intervals of 1 to 3 days, at a concentration of 0.5 ppm to 1.5 ppm.

5. The method of claim 3, wherein ivermectin is administered at intervals of 2 to 3 days, at a concentration of 1.5 ppm to 2.5 ppm.

* * * * *